(12) United States Patent
Hu et al.

(10) Patent No.: US 10,211,539 B2
(45) Date of Patent: Feb. 19, 2019

(54) RECONFIGURABLE ANTENNA

(71) Applicant: The University of Birmingham, Birmingham (GB)

(72) Inventors: Zhen Hua Hu, Birmingham (GB); Peter Hall, Birmingham (GB)

(73) Assignee: Smart Antenna Technologies Ltd., Birmingham (GB)

( * ) Notice: Subject to any disclaimer, the term of this patent is extended or adjusted under 35 U.S.C. 154(b) by 144 days.

(21) Appl. No.: 14/417,481

(22) PCT Filed: Jul. 12, 2013

(86) PCT No.: PCT/GB2013/051855
§ 371 (c)(1),
(2) Date: Jan. 26, 2015

(87) PCT Pub. No.: WO2014/020302
PCT Pub. Date: Feb. 6, 2014

(65) Prior Publication Data
US 2015/0194738 A1     Jul. 9, 2015

(30) Foreign Application Priority Data
Jul. 31, 2012   (GB) .................................. 1213558.8

(51) Int. Cl.
*H01Q 21/00*     (2006.01)
*H01Q 9/16*      (2006.01)
(Continued)

(52) U.S. Cl.
CPC ... *H01Q 21/0006* (2013.01); *G01N 33/48721* (2013.01); *H01Q 1/243* (2013.01);
(Continued)

(58) Field of Classification Search
CPC ...... H01C 21/0006; H01C 9/265; H01C 9/16; H01C 21/28; H01C 1/243; H01C 1/521; G01N 33/48721
See application file for complete search history.

(56) References Cited

U.S. PATENT DOCUMENTS 5,300,936 A    4/1994  Izadian
6,175,334 B1   1/2001  Vannatta et al.
(Continued)

FOREIGN PATENT DOCUMENTS

CN    1207004 A     2/1999
CN    101072061 A   11/2007
(Continued)

OTHER PUBLICATIONS

International Search Report and Written Opinion for corresponding PCT Application No. PCT/GB2013/051855, dated Sep. 10, 2013 (11 pgs.).
(Continued)

*Primary Examiner* — Jessica Han
*Assistant Examiner* — Michael Bouizza
(74) *Attorney, Agent, or Firm* — Shumaker & Sieffert, P.A.

(57) ABSTRACT

The present invention resides in a reconfigurable antenna. The antenna comprises a balanced antenna and an unbalanced antenna mounted on a supporting substrate, with both the balanced antenna and the unbalanced antenna located at the same end of the substrate. The antenna may be configured as a chassis antenna for use in a portable device or configured for Multiple-Input-Multiple-Output (MIMO) applications.

21 Claims, 12 Drawing Sheets

(51) Int. Cl.
*H01Q 1/24* (2006.01)
*H01Q 1/52* (2006.01)
*H01Q 9/26* (2006.01)
*H01Q 21/28* (2006.01)
*G01N 33/487* (2006.01)

(52) U.S. Cl.
CPC ............... *H01Q 1/521* (2013.01); *H01Q 9/16* (2013.01); *H01Q 9/265* (2013.01); *H01Q 21/28* (2013.01)

(56) References Cited

U.S. PATENT DOCUMENTS

| | | |
|---|---|---|
| 6,329,954 B1 | 12/2001 | Fuchs et al. |
| 6,879,294 B2 | 4/2005 | Yuanzhu |
| 6,909,401 B2 | 6/2005 | Rutfors et al. |
| 7,239,281 B2 | 7/2007 | Lu |
| 7,408,511 B2 | 8/2008 | Liu |
| 7,492,318 B2 | 2/2009 | Duzdar et al. |
| 9,190,719 B2 | 11/2015 | Kerselaers |
| 9,379,430 B2 | 6/2016 | Kerselaers |
| 2003/0137463 A1 | 7/2003 | Shimizu |
| 2003/0189519 A1* | 10/2003 | Rutfors ............... H01Q 21/28 343/702 |
| 2006/0227057 A1 | 10/2006 | Lu |
| 2007/0024513 A1* | 2/2007 | Sako ................. H01Q 21/28 343/727 |
| 2007/0176829 A1 | 8/2007 | Liu |
| 2008/0287084 A1* | 11/2008 | Krebs ................. H01Q 1/243 455/271 |
| 2009/0109104 A1 | 4/2009 | Ide et al. |
| 2010/0220022 A1 | 9/2010 | Yoon et al. |
| 2010/0265145 A1 | 10/2010 | Chung |
| 2010/0265146 A1* | 10/2010 | Montgomery ...... H01Q 1/243 343/722 |
| 2011/0221640 A1 | 9/2011 | Huber |
| 2012/0001811 A1 | 1/2012 | Yoo et al. |
| 2015/0311582 A1 | 10/2015 | Hu et al. |

FOREIGN PATENT DOCUMENTS

| | | |
|---|---|---|
| CN | 102655266 A | 9/2012 |
| CN | 102655267 A | 9/2012 |
| CN | 104769772 A | 7/2015 |
| DE | 20314442 U1 | 11/2003 |
| EP | 1772930 A1 | 11/2007 |
| EP | 2348576 A1 | 7/2011 |
| EP | 2479839 A1 | 7/2012 |
| GB | 2422723 A | 8/2006 |
| JP | 2008219661 A | 9/2008 |
| JP | 2009535942 A | 10/2009 |
| JP | 2008126857 A1 | 7/2010 |
| WO | 9966595 A1 | 12/1999 |
| WO | 2011124636 A1 | 10/2011 |
| WO | 2012072969 A1 | 6/2012 |

OTHER PUBLICATIONS

Examination Report from counterpart Application No. GB1220236.2, dated Jul. 21, 2015, 3 pp.
Office Action from U.S. Appl. No. 14/439,131, dated Oct. 6, 2016, 8 pp.
Office Action from U.S. Appl. No. 14/439,131, dated Mar. 17, 2017, 11 pp.
Notification of the First Office Action for CN Application No. 201380040774.0, dated Jun. 8, 2016, 9 pp.
Examination Report from application No. GB 1220236.2, dated Jul. 21, 2015, 3 pp.
International Search Report and Written Opinion from PCT Application No. PCT/GB2013/052838, dated Jan. 27, 2014, 8 pgs.
Response to Office Action dated Oct. 6, 2016, from U.S. Appl. No. 14/439,131, filed Feb. 6, 2017, 11 pp.
Notification of the First Office Action for CN Application No. 201380058388.4, dated Jun. 22, 2016, 12 pp.
Notification of the Second Office Action for CN Application No. 201380040774.0, dated Jan. 10, 2017, 15 pp.
CN Search Report for CN Application No. 201380058388.4, dated Jun. 14, 2016, 3 pp.
Bernhard, "Reconfigurable Antennas," Synthesis Lectures on Antennas, Lecture #4, published online Nov. 26, 2007, 74 pp.
Wallace, "Antenna Selection Guide," Application Note AN058, Texas Instruments, Oct. 5, 2010, 45 pp.
Response to Office Action dated Mar. 17, 2017, from U.S. Appl. No. 14/439,131, filed Jun. 15, 2017, 9 pp.
Notice of Allowance from U.S. Appl. No. 14/439,131, dated Jul. 14, 2017, 7 pp.
Japanese First Office Action for corresponding JP Application No. 2015-524839, 2018 (12 pgs.).

* cited by examiner

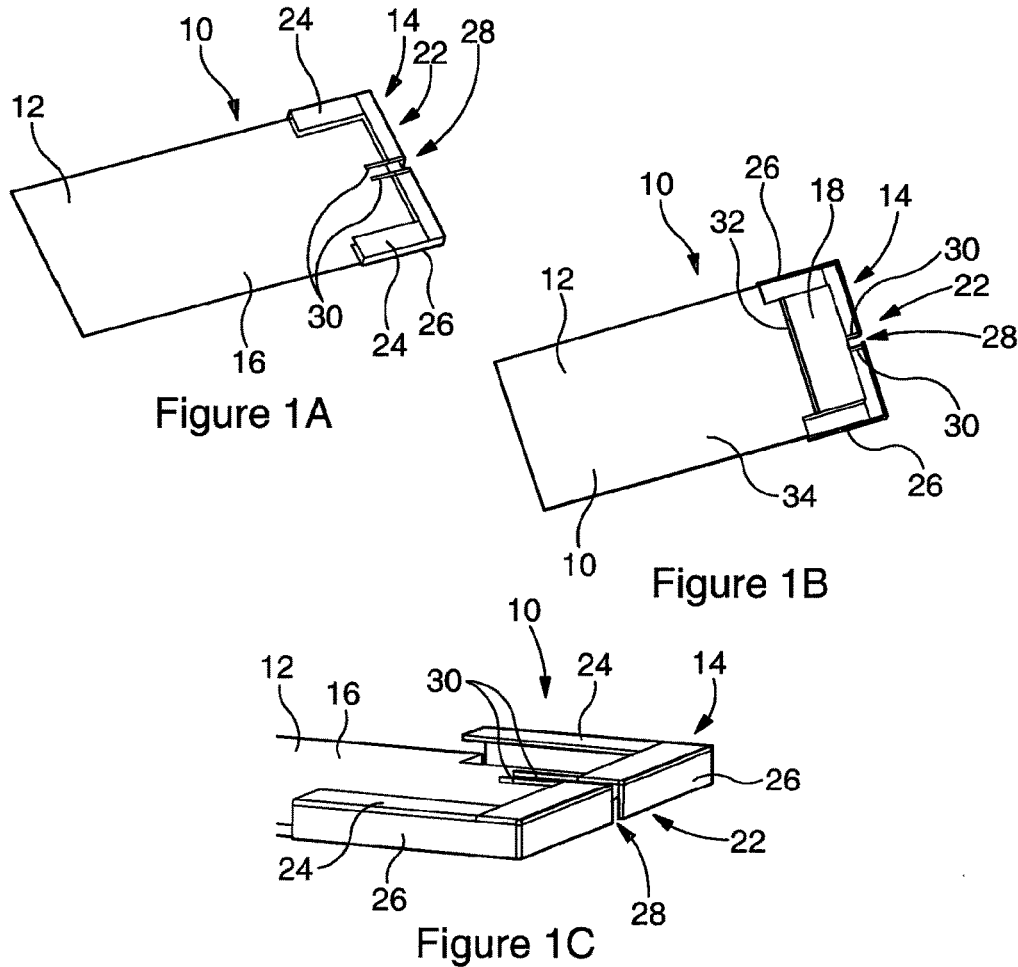
Figure 1A
Figure 1B
Figure 1C
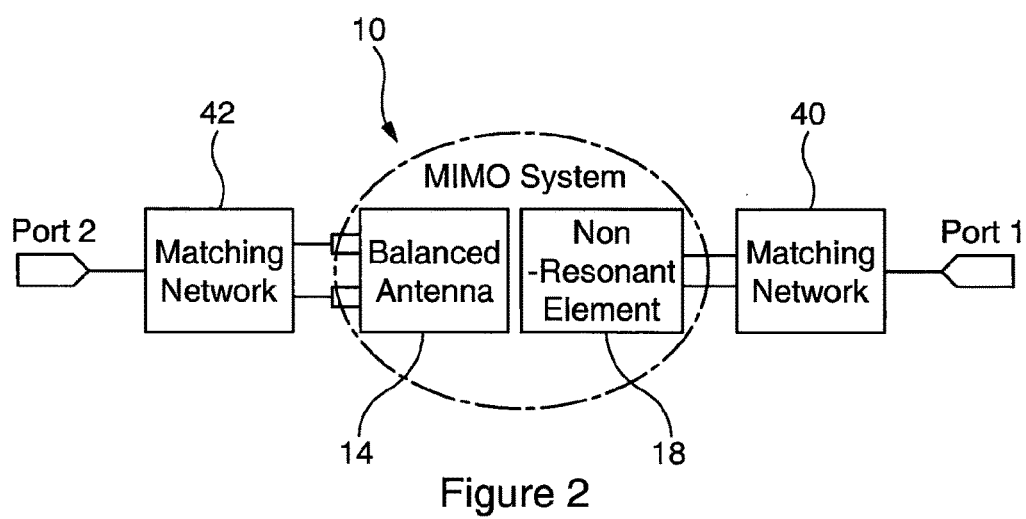
Figure 2

RECONFIGURABLE ANTENNA

This application is a national stage entry under 35 U.S.C. § 371 of PCT Application No. PCT/GB2013/051855, filed Jul. 12, 2013, which claims the benefit of Great Britain Application No. 1213558.8, filed Jul. 31, 2012. The entire contents of each of PCT Application No. PCT/GB2013/051855 and Great Britain Application No. 1213558.8 are incorporated herein by reference in their entirety.

FIELD OF THE INVENTION

The invention relates to a reconfigurable antenna. Particularly, but not exclusively, the invention relates to a reconfigurable multiple-input multiple-output (MIMO) antenna for use in a portable electronic device such as a mobile telephone, laptop, personal digital assistant (PDA) or radio.

BACKGROUND TO THE INVENTION

Multiple-input multiple-output (MIMO) wireless systems exploiting multiple antennas as both transmitters and receivers have attracted increasing interest due to their potential for increased capacity in rich multipath environments. Such systems can be used to enable enhanced communication performance (i.e. improved signal quality and reliability) by use of multi-path propagation without additional spectrum requirements. This has been a well-known and well-used solution to achieve high data rate communications in relation to 2G and 3G communication standards. For indoor wireless applications such as router devices, external dipole and monopole antennas are widely used. In this instance, high-gain, omni-directional dipole arrays and collinear antennas are most popular. However, very few portable devices with MIMO capability are available in the marketplace. The main reason for this is that, when gathering several radiators in a portable device, the small allocated space for the antenna limits the ability to provide adequate isolation between each radiator.

The applicants have described a first reconfigurable MIMO antenna in WO2012/072969. An embodiment is described in which the antenna comprises a balanced antenna located at a first end of a PCB and a two-port chassis-antenna located at an opposite second end of the PCB. However, in certain applications this configuration may not be ideal or even practical since it requires two separate areas in which to locate each antenna. However, as mentioned above this spacing was chosen to provide adequate isolation between each antenna structure.

An aim of the present invention is therefore to provide a reconfigurable antenna which helps to address the above-mentioned problems.

SUMMARY OF THE INVENTION

According to a first aspect of the present invention there is provided a reconfigurable antenna comprising: a balanced antenna and an unbalanced antenna mounted on a supporting substrate; wherein both the balanced antenna and the unbalanced antenna are located at the same end of the substrate.

Embodiments of the invention therefore provide a reconfigurable antenna which is located at one end of a supporting substrate (e.g. PCB) and which is therefore easily integrated into small portable devices such as conventional mobile telephones. The antenna itself may have a small, low profile and be relatively cheap to manufacture, for example, when compared to the reconfigurable MIMO antenna in WO2012/072969. The antenna may also offer good performance (i.e. high efficiency and gain), reduced specific absorption rate (SAR), a wide frequency covering range and high isolation between each radiator.

The balanced antenna and/or the unbalanced antenna may be non-resonant. For example, the unbalanced antenna may comprise a non-resonant element which is fed against a ground plane formed by or on the substrate. By contrast the balanced antenna may be fed against itself.

The antenna may further comprise one or more matching circuits arranged to tune the balanced antenna and/or the unbalanced antenna to a desired operating frequency. For example, the antenna may be configured to cover one or more of: DVB-H, GSM710, GSM850, GSM900, GSM1800, PCS1900, GPS1575, UMTS2100, Wifi®, Bluetooth®, LTE, LTA and 4G frequency bands.

In certain embodiments, the unbalanced antenna (e.g. non-resonant element) may be located adjacent to; at least partially enclosed by; within the footprint of; or transversely aligned with at least a portion of the balanced antenna.

The balanced antenna and the unbalanced antenna may be provided with substantially centrally located feed lines. This is advantageous in ensuring that the antenna has high performance.

The supporting substrate may be constituted by a printed circuit board (PCB).

The unbalanced antenna may comprise at least a portion which is etched onto the substrate. Alternatively, the unbalanced antenna may comprise at least a portion which is provided on a separate structure which is attached to the substrate.

The shape and configuration of the unbalanced antenna is not particularly limited and may be designed for a specific application and/or desired performance criteria. Similarly, the shape and configuration of the balanced antenna is not particularly limited and may be designed for a specific application and/or desired performance criteria.

In one embodiment, the unbalanced antenna may be rectangular. In another embodiment the unbalanced antenna may be bracket-shaped, for example, having a first element substantially parallel to the substrate and a second element substantially perpendicular to the substrate.

In one embodiment, the balanced antenna may comprise two inwardly facing L-shaped arms. In other embodiments, the balanced antenna may be bracket-shaped (e.g. with each arm having at least one perpendicular element) or constituted by a printed dipole.

The balanced antenna may be located above the substrate or around (i.e. outside of) the substrate. In certain embodiments, the substrate may be substantially rectangular but with a cut-out located beneath the balanced antenna.

The balanced antenna and the unbalanced antenna may be provided on opposite surfaces of the substrate (although still at the same end thereof). In certain embodiments, the balanced antenna and the unbalanced antenna may be transversely separated by the thickness of the substrate alone.

The substrate may have a ground plane printed on a first surface thereof. The unbalanced antenna also may be provided on the first surface and may be spaced from the ground plane by a gap.

Multiple matching circuits may be provided for each of the balanced antenna and the unbalanced antenna. Different modes of operation may be available by selecting different matching circuits for the balanced antenna and/or the unbalanced antenna.

Switches may be provided to select the desired matching circuits for a particular mode of operation (i.e. a particular frequency band or bands).

Each matching circuit may comprise at least one variable capacitor to tune the frequency of the associated balanced antenna or unbalanced antenna over a particular frequency range. The variable capacitor may be constituted by multiple fixed capacitors with switches, varactors or MEMs capacitors.

The matching circuits associated with the unbalanced antenna may be coupled to a first signal port and the matching circuits associated with the balanced antenna may be coupled to a second signal port.

Each signal port and/or matching circuit may be associated with a different polarisation. For example, a 90 degree phase difference may be provided between each port/matching circuit at a desired operating frequency.

The antenna may further comprising a control system which is connected to each port and which comprises a control means for selecting a desired operating mode.

The substrate may be of any convenient size and in one embodiment may have a surface area of approximately 116×40 mm$^2$ so that it can easily be accommodated in a conventional mobile device. It will be understood that the thickness of the substrate is not limited but will typically be a few millimeters thick (e.g. 1 mm, 1.5 mm, 2 mm or 2.5 mm).

The reconfigurable antenna of the present invention may be configured as a chassis antenna for use in a portable device. The antenna may be configured for Multiple-Input-Multiple-Output (MIMO) applications.

BRIEF DESCRIPTION OF THE DRAWINGS

Certain embodiments of the present invention will now be described with reference to the accompanying drawings in which:

FIG. 1A shows a top perspective view of an antenna according to a first embodiment of the present invention mounted on a PCB;

FIG. 1B shows an underside perspective view of the antenna and PCB shown in FIG. 1A;

FIG. 1C shows an enlarged end perspective view of the antenna and PCB shown in FIG. 1A;

FIG. 2 shows a block diagram of the circuitry associated with the antenna of FIGS. 1A through 1C;

DETAILED DESCRIPTION OF CERTAIN EMBODIMENTS

Figure 3:
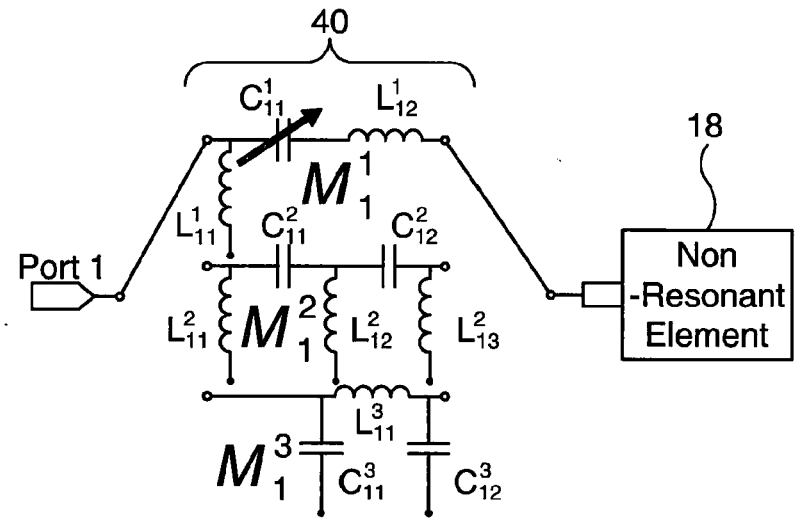
FIG. 3 shows a circuit diagram illustrating the matching circuit arrangement for the non-resonant element in the antenna of FIG. 2.

With reference to FIGS. 1A, 1B and 1C there is shown an antenna 10 according to a first embodiment of the present invention, mounted on a PCB 12. The antenna 10 comprises a balanced antenna 14 mounted on a first surface 16 of the PCB 12 and an unbalanced antenna in the form of a non-resonant element 18 mounted on an opposite second surface 20 of the PCB 12. Both the balanced antenna 14 and the non-resonant element 18 are located at the same end 22 of the PCB 12.

Figure 10:
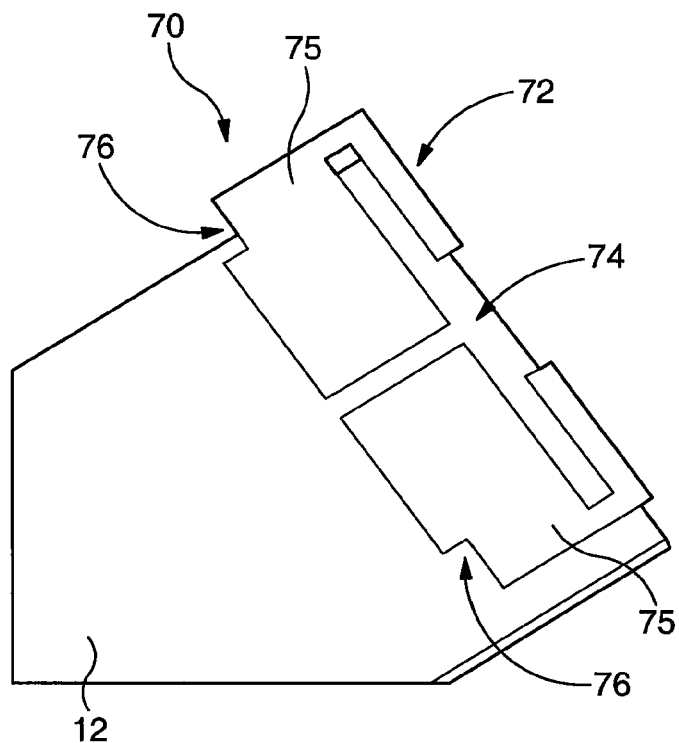
FIG. 10 shows an enlarged top perspective view of a forth embodiment of the present invention, which comprises a printed dipole balanced antenna.

The balanced antenna 14 comprises two inwardly facing planar L-shaped arms 24 which are mounted above and parallel to the plane of the PCB 12. As best illustrated in FIG. 10, each arm 24 is mounted at its outer edge on an orthogonal support 26 which extends from a long edge of the PCB 12, past the end 22 of the PCB 12 and in towards the centre of the end 22. In other words, the balanced antenna 14 is suspended above a U-shaped cut-out around the end 22 of the PCB 12. Notably, the supports 26 and the arms 24 do not meet in the centre of the end 22 but define a gap 28 therebetween. Two feed lines 30 (extending from the first surface 16) are provided towards the centre of the balanced antenna 14, one on each side of the gap 28, to respectively feed each arm 24.

The non-resonant element 18 is constituted by a rectangular metal etching over the end 22 of the PCB 12 which is surrounded by the balanced antenna 14. However, as shown in FIG. 1B, the non-resonant element 18 stops short of the end of the U-shaped cut-out and a gap 32 is provided between the non-resonant element 18 and the remainder of the second surface 20 which constitutes a ground plane 34. Although not shown, the non-resonant element 18 is provided with a central feed line.

FIG. 2 shows a block diagram of the circuitry associated with the antenna 10. Accordingly, it can be seen that the non-resonant element 18 is fed through Port 1 via a matching circuit 40 and the balanced antenna 14 is fed through Port 2 via a matching circuit 42. As will be explained below, the external matching circuits 40, 42 are required to achieve a wide operating frequency range.

FIG. 3 shows a circuit diagram illustrating the matching circuit 40 for the non-resonant element 18. In this embodiment, the matching circuit 40 comprises three alternative matching circuits denoted $M_1^1$, $M_1^2$ and $M_1^3$, which can be individually selected to provide three different modes of operation (Mode 1, Mode 2 and Mode 3, respectively). Consequently, each matching circuit $M_1^1$, $M_1^2$ and $M_1^3$ can be selected by switches via a control system (not shown) such that Port 1 is connected to the non-resonant element 18 via the desired matching circuit to give the mode of operation required. In the embodiment shown, matching circuit $M_1^1$ is selected and the non-resonant element 18 is configured for operation in Mode 1.

Matching circuit $M_1^1$ comprises a first inductor $L_{11}^1$ connected in parallel to a variable capacitor $C_{11}^1$ which, in turn, is connected to a second inductor $L_2^1$. Matching circuit $M_1^2$ comprises a first inductor $L_{11}^2$ connected in parallel to a first capacitor $C_{11}^2$, which is connected in parallel to a second inductor $L_{12}^2$ and in series to a second capacitor $C_{12}^3$, which is then connected in parallel to a third inductor $L_{13}^2$. Matching circuit $M_1^3$ comprises a first capacitor $C_{11}^3$ connected in parallel to a first inductor $L_{11}^3$, which is then connected in parallel to a second capacitor $C_{12}^3$.

Figure 4:
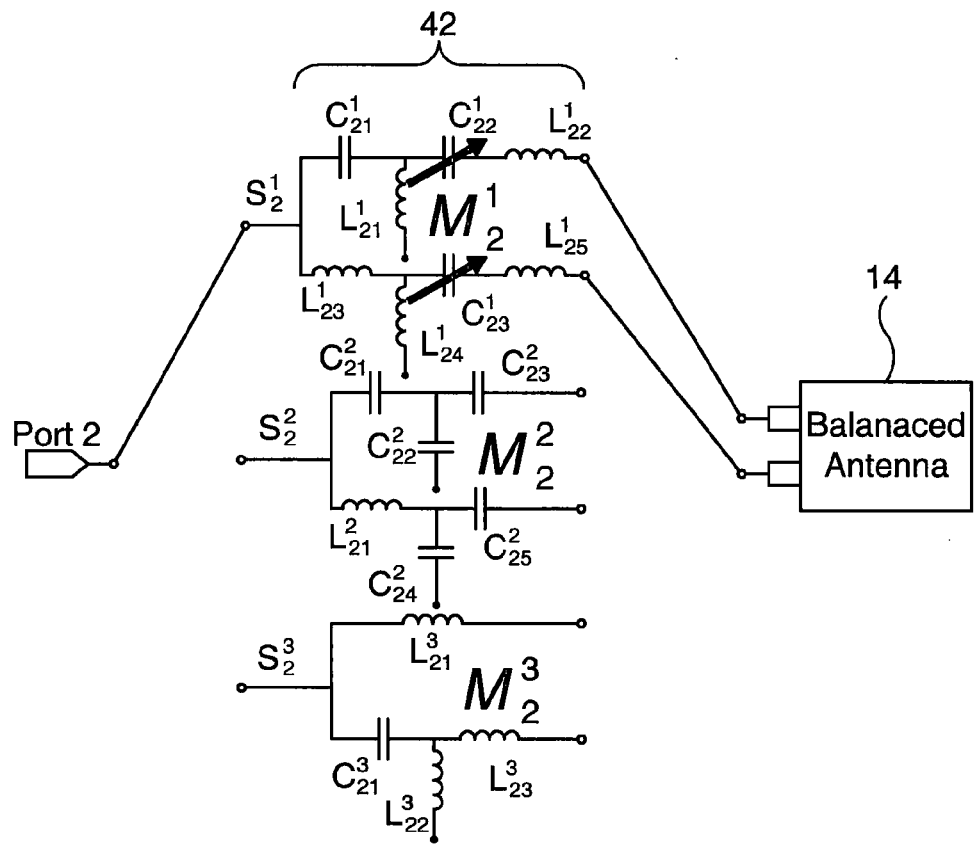
FIG. 4 shows a circuit diagram illustrating the matching circuit arrangement for the balanced antenna in the antenna of FIG. 2.

FIG. 4 shows a circuit diagram illustrating the matching circuit arrangement 42 for the balanced antenna 14. In this embodiment, the matching circuit 42 comprises three alternative matching circuits denoted $M_2^1$, $M_2^2$ and $M_2^3$, which can also be individually selected to provide three different modes of operation (Mode 1, Mode 2 and Mode 3, respectively). Consequently, each matching circuit $M_2^1$, $M_2^2$ and $M_2^3$ can be selected by switches via a control system (not shown) such that Port 2 is connected to the balanced antenna 14 via the desired matching circuit to give the mode of operation required. In the embodiment shown, matching circuit $M_2^1$ is selected and the balanced antenna 14 is configured for operation in Mode 1.

Matching circuit $M_2^1$ comprises a splitter $S_2^1$ which splits the signal from Port 2 into a first branch and a second branch. The first branch comprises a first capacitor $C_{21}^1$ connected in parallel to a first inductor $L_{21}^1$ and in series to a second (variable) capacitor $C_{22}^1$ and a second inductor $L_{22}^1$. The second branch comprises a third inductor $L_{23}^1$ connected in parallel to a fourth inductor $L_{24}^1$ and in series to a third (variable) capacitor $C_{23}^1$ and a fifth inductor $L_{25}^1$.

Matching circuit $M_2^2$ comprises a splitter $S_2^2$ which splits the signal from Port 2 into a first branch and a second branch. The first branch comprises a first capacitor $C_{21}^2$ connected in parallel to a second capacitor $C_{22}^2$ and in series to a third capacitor $C_{23}^2$.

The second branch comprises a first inductor $L_{21}^2$ connected in parallel to a fourth capacitor $C_{24}^2$ and in series to a fifth capacitor $C_{25}^2$.

Matching circuit $M_2^3$ comprises a splitter $S_2^3$ which splits the signal from Port 2 into a first branch and a second branch. The first branch comprises a first series inductor $L_{21}^3$. The second branch comprises a first capacitor $C_{21}^3$ connected in parallel to a second inductor $L_{22}^3$ and in series to a third inductor $L_{23}^3$.

In summary, there is one variable capacitor in matching circuit $M_1^1$ and two variable capacitors in matching circuit $M_2^1$. These variable capacitors may comprise several fixed capacitors with switches, varactors, MEMs capacitors or the like.

The matching circuits of FIGS. 3 and 4 are designed to cover three LTE frequency bands (i.e. 698 MHz to 960 MHz, 1710 MHz to 2170 MHz and 2300 MHz to 2690 MHz) as well as other common required frequency ranges. More specifically, when operating in Mode 1 (i.e. matching circuits $M_1^1$ and $M_2^1$ are selected), Port 1 and Port 2 can cover the LTE low band which is from 698 MHz to 960 MHz plus GSM710, GSM850 and GSM900. When operating in Mode 2 (i.e. matching circuits $M_1^2$ and $M_2^2$ are selected), Port 1 and Port 2 can cover the LTE mid band which is from 1710 MHz to 2170 MHz plus UMTS2100. When operating in Mode 3 (i.e. matching circuits $M_1^3$ and $M_2^2$ are selected), Port 1 can cover LTE high band 2300 MHz to 2690 MHz, WiFi®, and Bluetooth® while Port 2 can cover most of LTE high band 2500 MHz to 2690 MHz. It will be understood that other frequency bands can be covered by including additional matching circuits which are selected by switches to provide further modes of operation.

Figure 5:
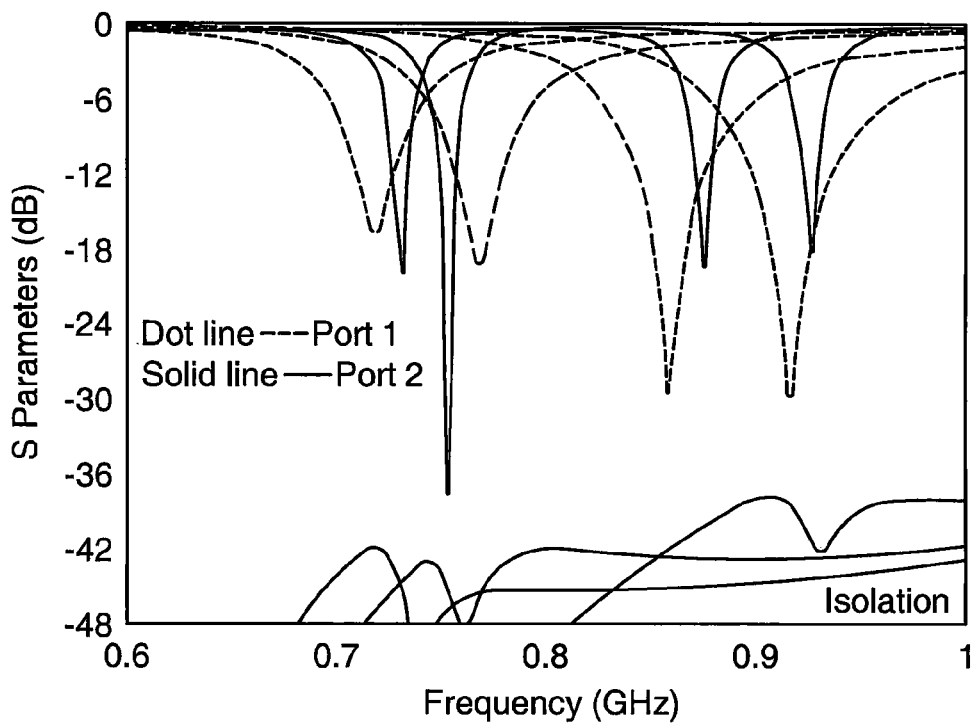
FIG. 5 shows a graph of return loss against frequency for the antenna of FIGS. 1A to 4, when operating in mode 1 (i.e. when matching circuits $M_1^1$ and $M_2^1$ are selected and the variable capacitors are varied.

FIG. 5 shows a graph of return loss against frequency for the antenna of FIGS. 1A to 4, when operating in Mode 1 (i.e. when matching circuits $M_1^1$ and $M_2^1$ are selected and the variable capacitors are varied. Accordingly, by varying the capacitor value, it is possible to tune the resonant frequencies of Port 1 and Port 2 to cover the band between approximately 698 MHz and 960 MHz with an isolation of at least 37 dB over the operating band.

Figure 6:
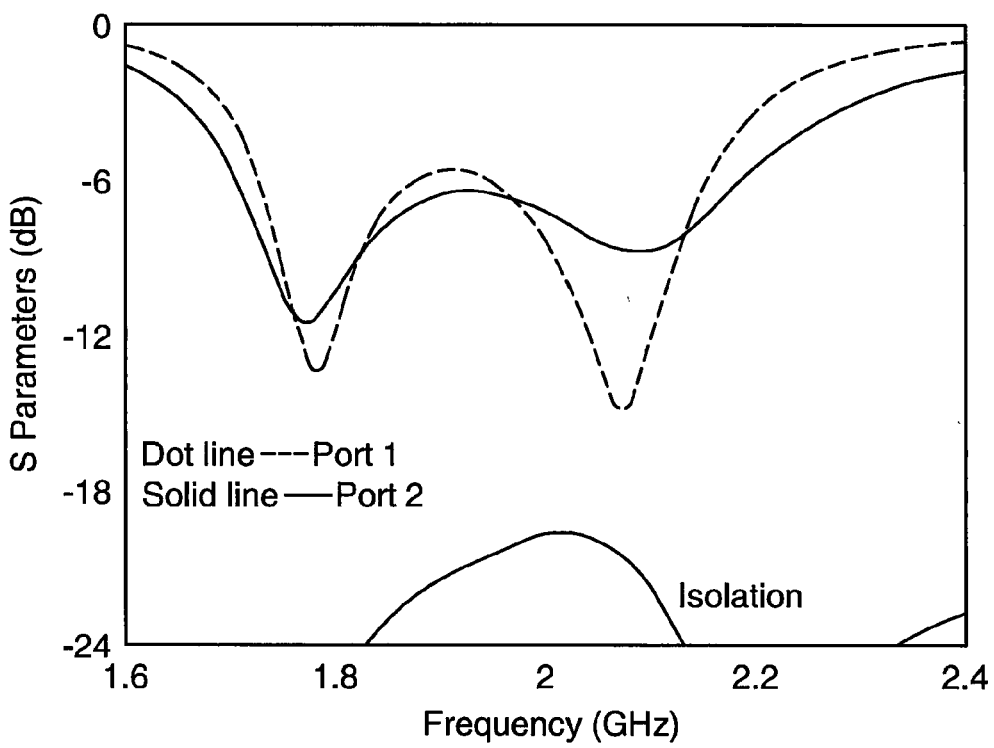
FIG. 6 shows a graph of return loss against frequency for the antenna of FIGS. 1A to 4, when operating in mode 2 (i.e. when matching circuits $M_1^2$ and $M_2^2$ are selected)

FIG. 6 shows a graph of return loss against frequency for the antenna of FIGS. 1A to 4, when operating in mode 2 (i.e. when matching circuits $M_1^2$ and $M_2^2$ are selected). Accordingly, it is possible to cover the frequencies between approximately 1710 MHz and 2170 MHz with an isolation of at least 20 dB over the operating band.

Figure 7:
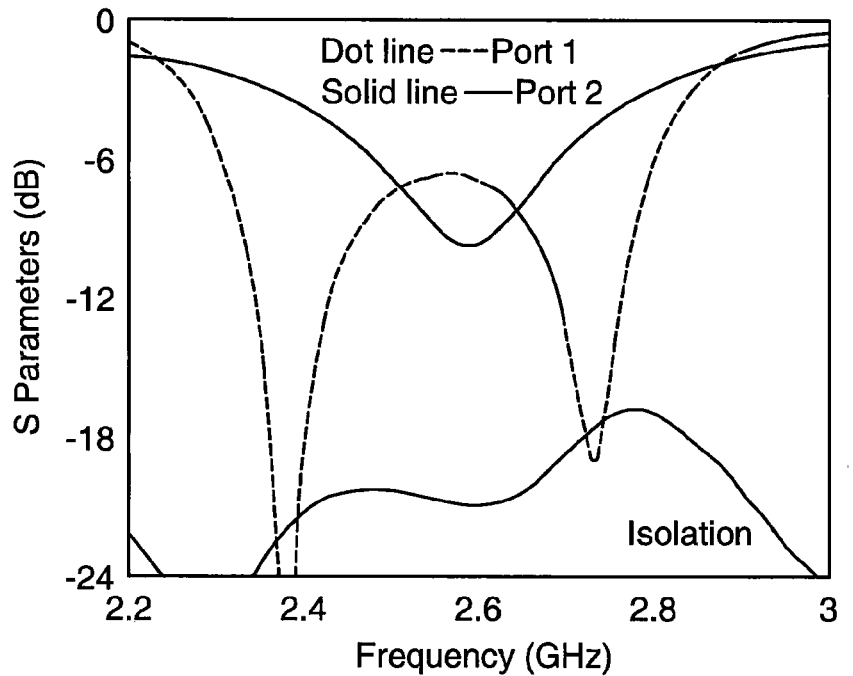
FIG. 7 shows a graph of return loss against frequency for the antenna of FIGS. 1A to 4, when operating in mode 3 (i.e. when matching circuits $M_1^3$ and $M_2^3$ are selected)

FIG. 7 shows a graph of return loss against frequency for the antenna of FIGS. 1A to 4, when operating in mode 3 (i.e. when matching circuits $M_1^3$ and $M_2^3$ are selected). Accordingly, it is possible to cover the frequencies between approximately 2300 MHz and 2690 MHz with an isolation of at least 20 dB over the operating band.

It should be noted that there is no tuning circuit for modes 2 and 3, thus no need to use variable capacitors, as the matching circuits with fixed components can cover the required frequency bands.

Figure 8:
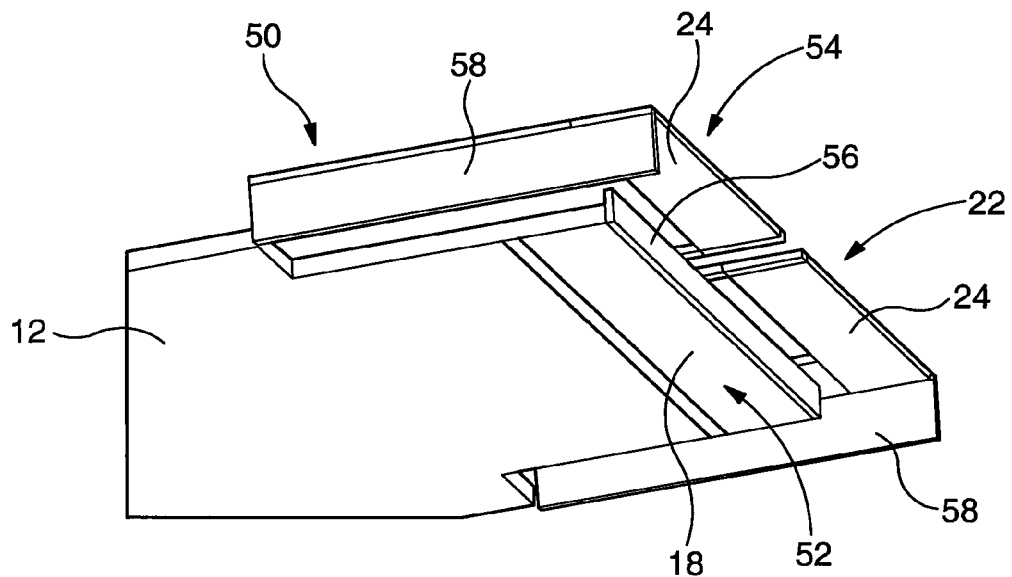
FIG. 8 shows an enlarged underside perspective view of a second embodiment of the present invention, which comprises a bracket-shaped non-resonant element and a "semi-bracket" shaped balanced antenna.

FIG. 8 shows an enlarged underside perspective view of an antenna 50 according to a second embodiment of the present invention. The antenna 50 is substantially similar to that shown in FIGS. 1A through 1C except that the structure of the non-resonant element 52 and the balanced antenna 54 is slightly different. More specifically, the non-resonant element 52 is bracket-shaped and comprises an elongate perpendicular end portion 56 mounted along the end 22 of a portion constituting the planar non-resonant element 18. Furthermore, the balanced antenna 54 is "semi-bracket" shaped in that the supports 58 for the L-shaped arms 24 are only provided along the long edge of the PCB 12 and do not extend inwardly towards the centre of the end 22.

Figure 9:
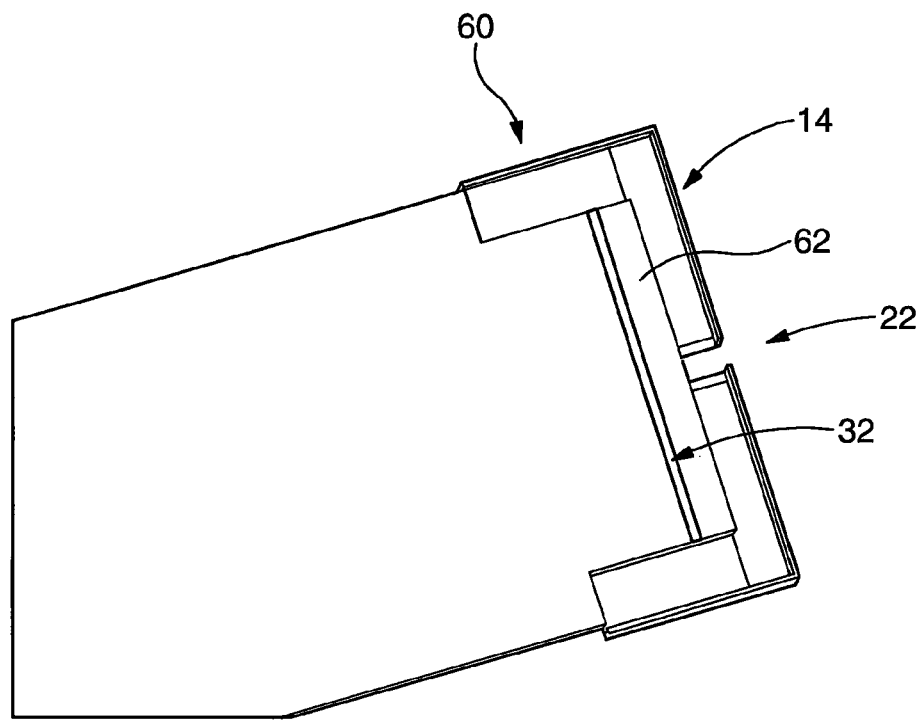
FIG. 9 shows an enlarged underside perspective view of a third embodiment of the present invention, which comprises a narrower non-resonant element to that shown in FIG. 1B.

FIG. 9 shows an enlarged underside perspective view of an antenna 60 according to a third embodiment of the present invention. The antenna 60 is substantially similar to that shown in FIGS. 1A through 1C except that the non-resonant element 62 is approximately half the width of the non-resonant element 18. Thus, the gap 32 is closer to the end 22 than to the end of the U-shaped cut-out beneath the balanced antenna 14.

FIG. 10 shows an enlarged top perspective view of an antenna 70 according to a forth embodiment of the present invention. The antenna 70 is substantially similar to that shown in FIGS. 1A through 1C except that the balanced antenna 72 is constituted by a printed dipole having a central substantially T-shaped cut-out 74 separating each arm 75 of the dipole and a small rectangular cut-out 76 at the extreme end of each arm 24, adjacent the long edge of the PCB 12. There is also no cut-out in the PCB 12. It will be noted that the distance between the balanced antenna 72 and the PCB 12 will directly affect the efficiency of the antenna 70. Thus, the balanced antenna 72 is supported at an appropriate distance above the PCB 12 by Rohacell™ foam or the like (not shown).

Figure 11:
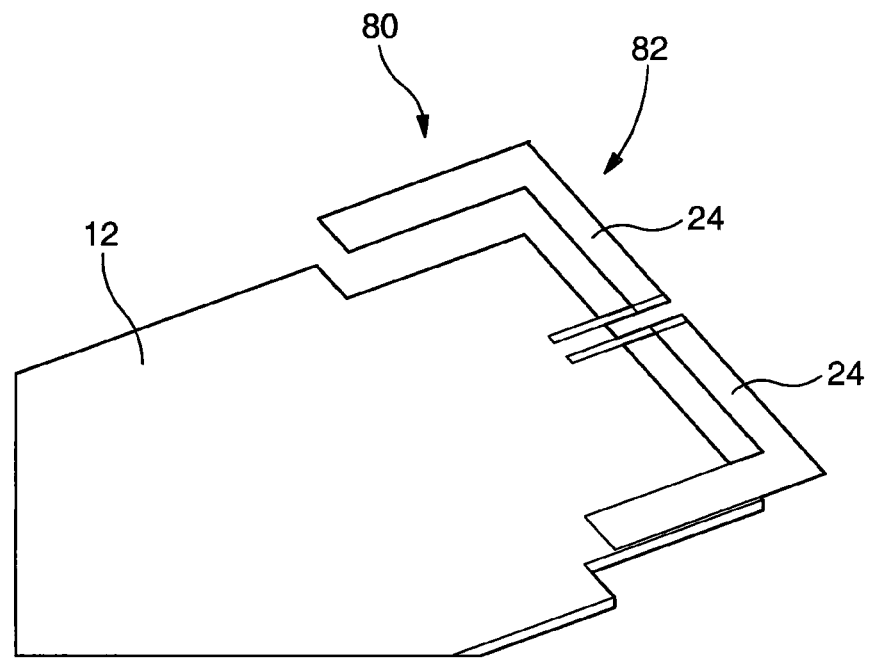
FIG. 11 shows an enlarged top perspective view of a fifth embodiment of the present invention, which comprises an L-shaped printed dipole balanced antenna.

FIG. 11 shows an enlarged top perspective view of an antenna 80 according to a fifth embodiment of the present invention. The antenna 80 is substantially similar to that shown in FIGS. 1A through 1C except that the balanced antenna 82 is constituted by an L-shaped printed dipole such that the arms 24 are no longer mounted on supports 26 but are instead mounted above the PCB 12 by foam supports or the like (not shown).

Figure 12:
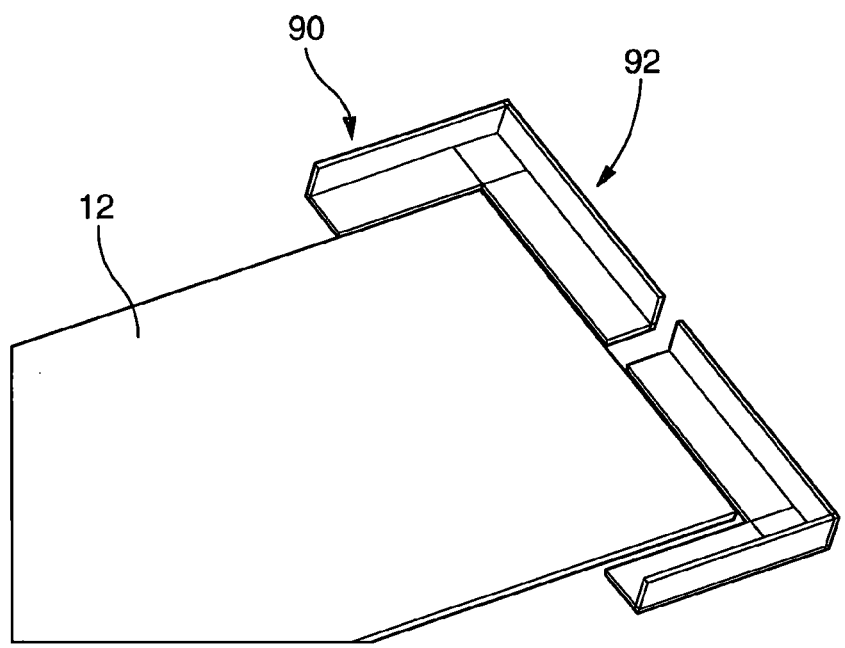
FIG. 12 shows an enlarged top perspective view of a sixth embodiment of the present invention, which comprises a balanced antenna provided around the outside of the PCB.

FIG. 12 shows an enlarged top perspective view of an antenna 90 according to a sixth embodiment of the present invention. The antenna 90 is substantially similar to that shown in FIGS. 1A through 1C except that the balanced antenna 92 is provided around the outside of the PCB 12 and there is no cut-out provided in the PCB 12. As per FIGS. 10 and 11, the balanced antenna 92 is mounted to the PCB 12 by foam supports or the like (not shown).

Figure 13A:
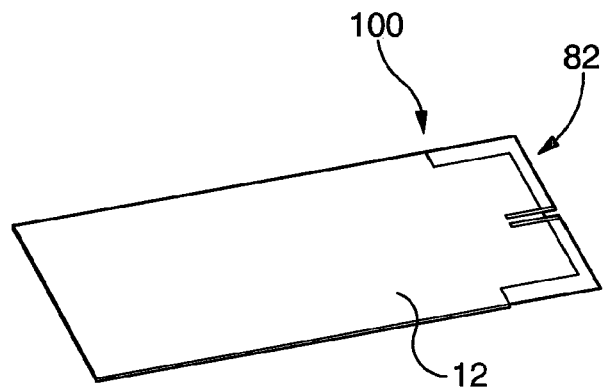
FIG. 13A shows top perspective view of an antenna according to a seventh embodiment of the present invention, comprising the balanced antenna shown in FIG. 11 and the non-resonant element shown in FIG. 9.
Figure 13B:
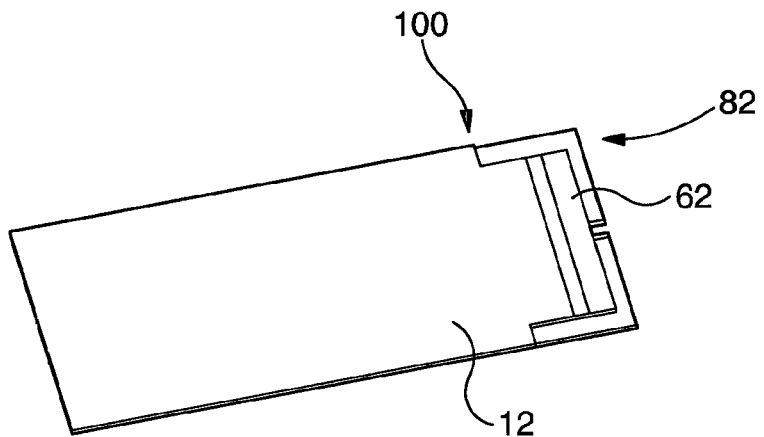
FIG. 13B shows an underside perspective view of the antenna shown in FIG. 13A.
Figure 13C:
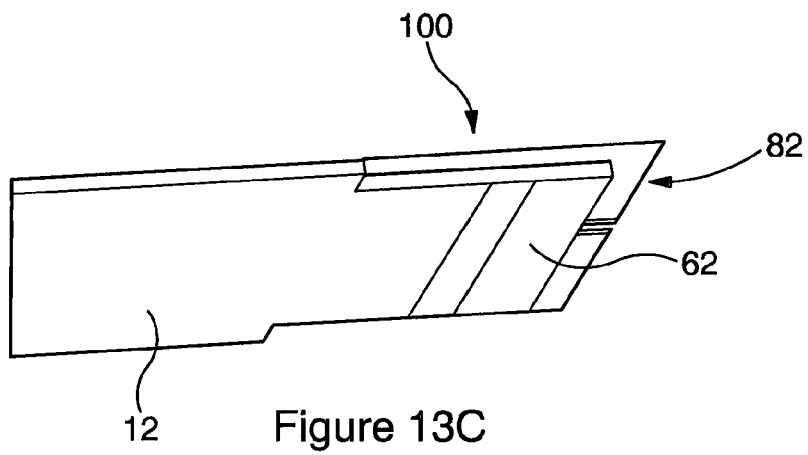
FIG. 13C shows an enlarged end underside perspective view of the antenna shown in FIG. 13A.

FIGS. 13A, 13B and 13C show an antenna 100 according to a seventh embodiment of the present invention. The antenna 100 comprises the balanced antenna 82 of FIG. 11 and the non-resonant element 62 of FIG. 9. In this embodiment, the distance between the balanced antenna 82 and the non-resonant element 62 is the only the thickness of the PCB 12 (i.e. no additional support is provided).

Figure 14:
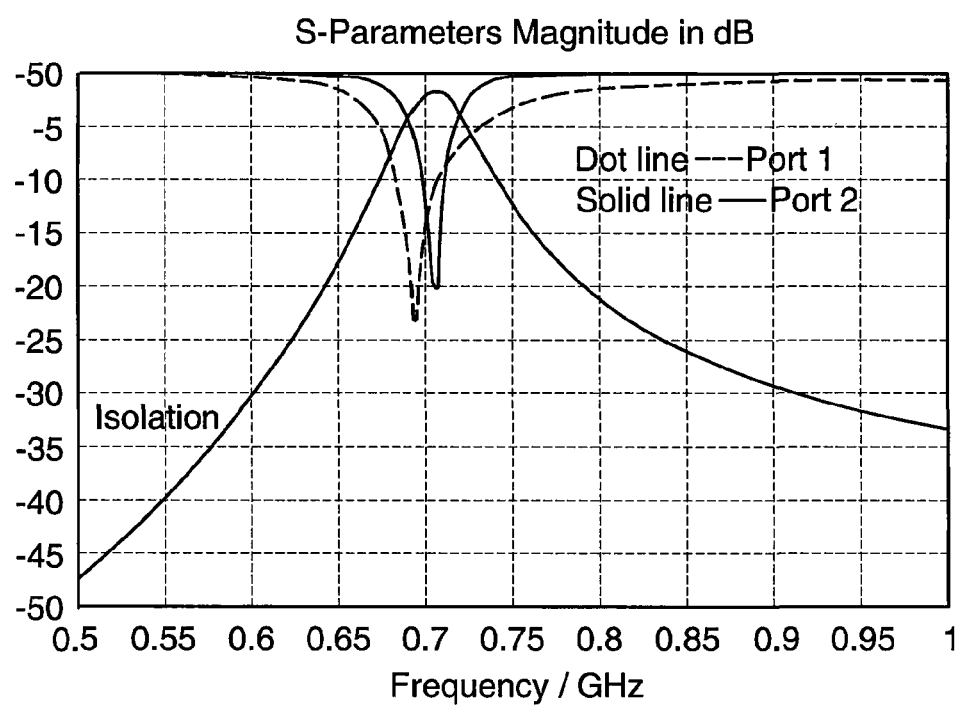
FIG. 14 shows a graph of return loss against frequency for the antenna of FIGS. 1A to 2, when each port is connected to a non-optimised matching circuit and the isolation between the ports is poor.
Figure 15B:
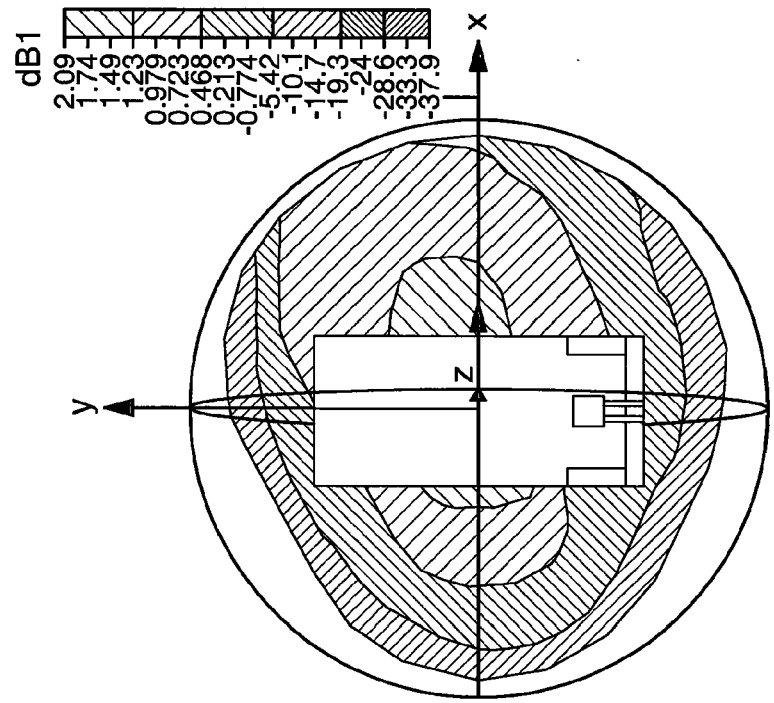
FIG. 15B shows the radiation pattern for port 2 when operating as illustrated in FIG. 14.
Figure 15A:
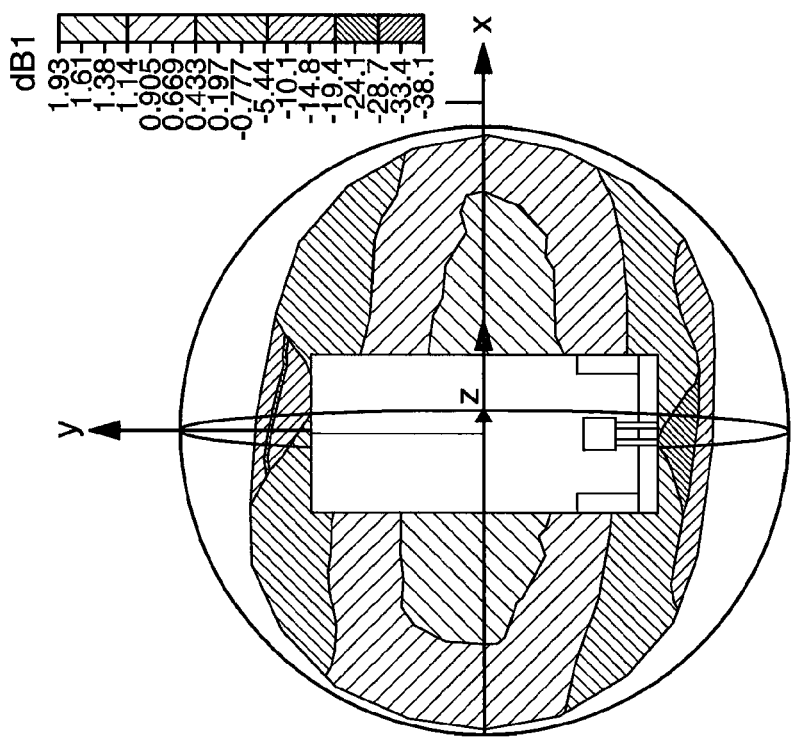
FIG. 15A shows the radiation pattern for port 1 when operating as illustrated in FIG. 14.

FIG. 14 shows a graph of return loss against frequency for the antenna of FIGS. 1A to 2, when each port (Port 1 and Port 2) is connected, respectively, to a non-optimised matching circuit 40, 42 and the isolation between the ports is poor (about 1 dB at the operating frequency which is around 732 MHz for each port). The Applicants have determined that the poor isolation in this case can be explained in relation to the signal polarisation. FIGS. 15A and 15B show, respectively, the radiation patterns for Port 1 and Port 2, when operating as illustrated in FIG. 14. Although the directivity for each port is slightly different, the polarisation in each case is in the same plane (the ZX plane, as illustrated) and it is believed that this causes the poor isolation shown in FIG. 14.

Figure 16:
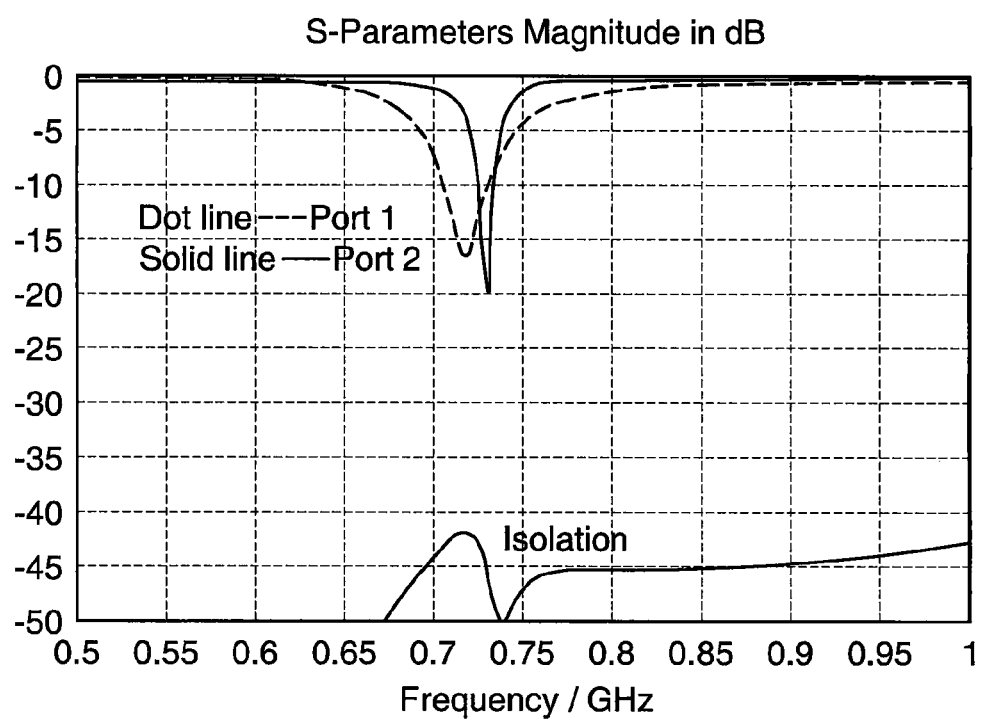
FIG. 16 shows a graph of return loss against frequency for the antenna of FIGS. 1A to 2, when each port is connected to an optimised matching circuit and the isolation between the ports is good.
Figure 17B:
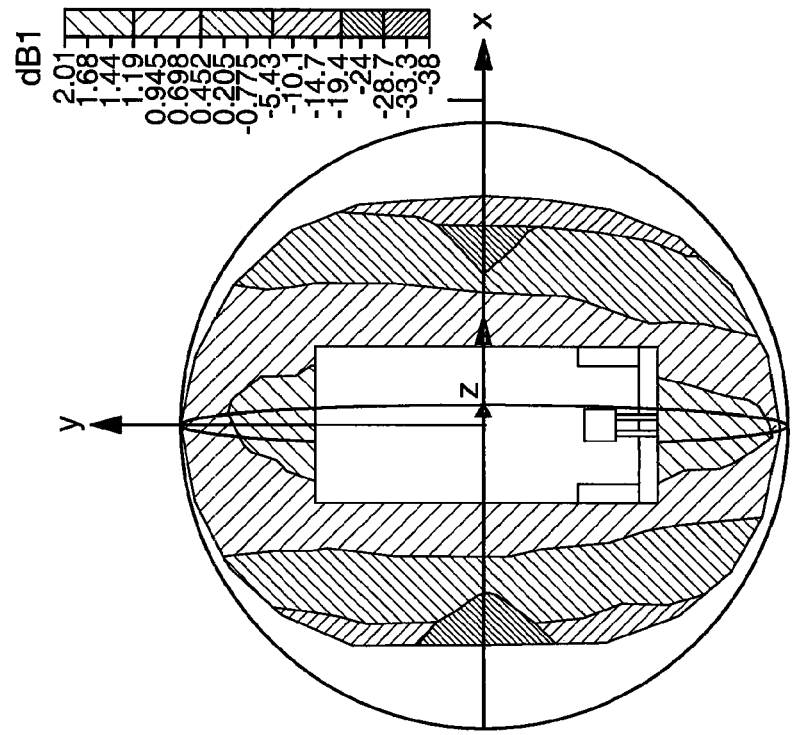
FIG. 17B shows the radiation pattern for port 2 when operating as illustrated in FIG. 16.
Figure 17A:
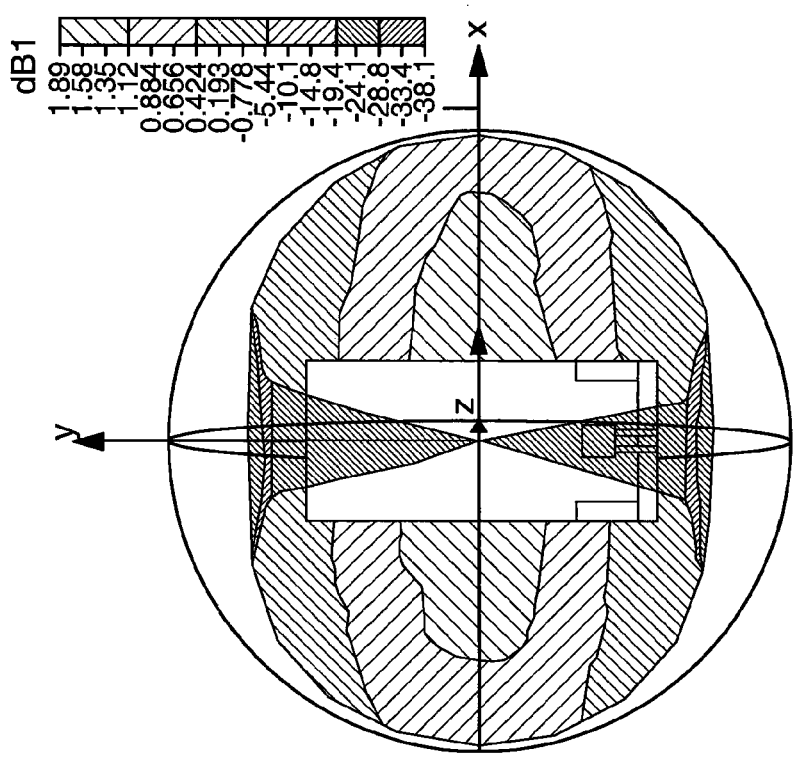
FIG. 17A shows the radiation pattern for port 1 when operating as illustrated in FIG. 16.

FIG. 16 shows a graph of return loss against frequency for the antenna of FIGS. 1A to 2, when each port (Port 1 and Port 2) is connected, respectively, to an optimised matching circuit 40, 42 and the isolation between the ports is good (more than 40 dB at the operating frequency which is around 732 MHz for each port). The high isolation in FIG. 16 can be explained from the radiation patterns for both ports shown, respectively, in FIGS. 17A and 17B. More specifically, FIG. 17A shows that the polarisation for Port 1 is in the ZX plane and the polarisation for Port 2 is in the ZY plane. The polarisations therefore have approximately a 90 degree phase difference which results in each port being highly isolated, as shown in FIG. 16.

The Applicants have therefore determined that high isolation between the ports can be achieved by introducing a phase difference (of e.g. 90 degrees) with respect to the polarisation of the signals from each port at the operating frequency. They also believe that the nature of the matching circuits themselves, and the number of components employed are much less critical in terms of isolation than the polarisation states. High performance is also possible as a result of the fact that both the balanced antenna and the unbalanced antenna are located at the same end of the PCB with the unbalanced antenna being located under or in the middle of the balanced antenna, the feed lines for both antennas being positioned at the middle of each antenna and each antenna being connected to a respective matching circuit.

Figure 18A:
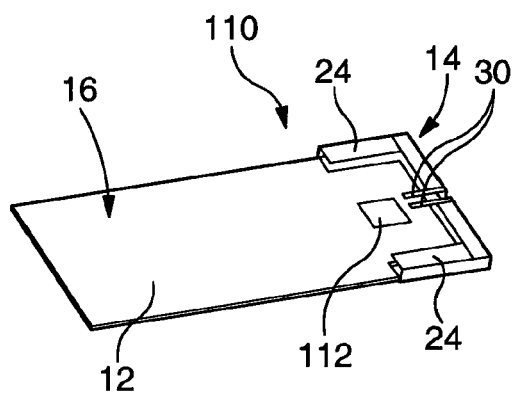
FIG. 18A shows a top perspective view of an antenna according to a further embodiment of the present invention, which is similar to that shown in FIG. 1A but wherein the balanced antenna connected to a floating ground plane.
Figure 18B:
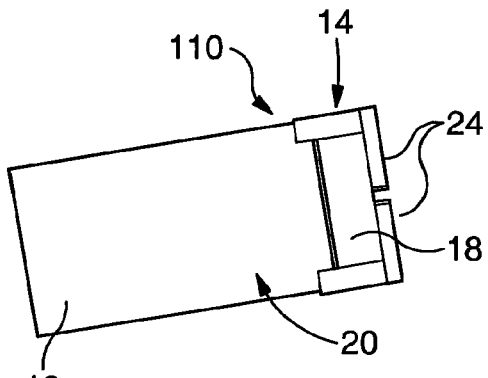
FIG. 18B shows a rear view of the antenna in FIG. 18A.

FIGS. 18A and 18B show an antenna 110 according to a further embodiment of the present invention, which is similar to that shown in FIG. 1A but wherein the balanced antenna 14 is connected to a floating ground plane 112. The floating ground plane 112 is constituted by a rectangular metal patch located on the first surface 16 of the PCB 12 generally centrally below the feed lines 30. Although not shown, the matching circuit configured to excite the symmetrical arms 24 of the balanced antenna 14 is located on the floating ground plane 112. As per FIG. 1B, the unbalanced antenna in the form of the non-resonant element 18 is mounted on the opposite second surface 20 of the PCB 12. The non-resonant element 18 is connected to a matching circuit on the PCB 12. As explained previously, high isolation between the ports for the balanced antenna and the unbalanced antenna is achieved by optimising the matching circuits of each antenna to provide a 90-degree difference in polarisation orientation. The circuit designs and the results for the antenna 110 are as shown in FIGS. 2 to 7.

Figure 19A:
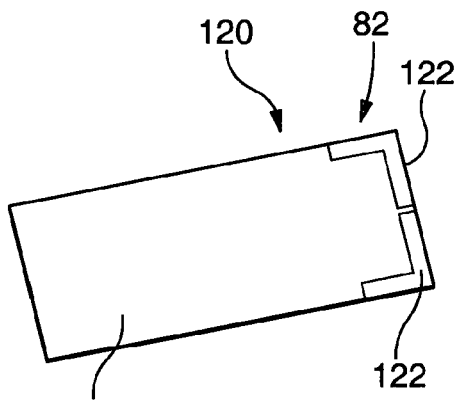
FIG. 19A shows a top perspective view of an antenna according to a further embodiment of the present invention, which is similar to that shown in FIGS. 13A-13C but wherein one of the symmetrical arms of the balanced antenna constitutes a floating ground plane for the other symmetrical arm.
Figure 19B:
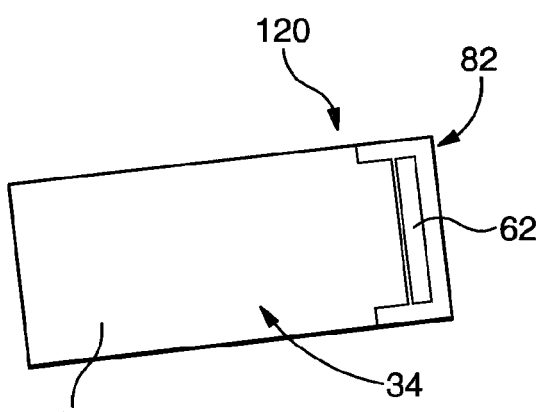
FIG. 19B shows a rear view of the antenna in FIG. 19A.

FIGS. 19A and 19B show an antenna 120 according to a further embodiment of the present invention, which is similar to that shown in FIGS. 13A-13C but wherein one of the symmetrical arms 122 of the balanced antenna 82 constitutes a floating ground plane for the other symmetrical arm 122. Although not shown, the matching circuit configured to excite the balanced antenna 82 is located on the symmetrical arm 122 constituting the floating ground plane. In relation to FIG. 19B, the non-radiating element 62 is connected to a matching circuit on the ground plane 34 of the PCB 12.

Figure 20:
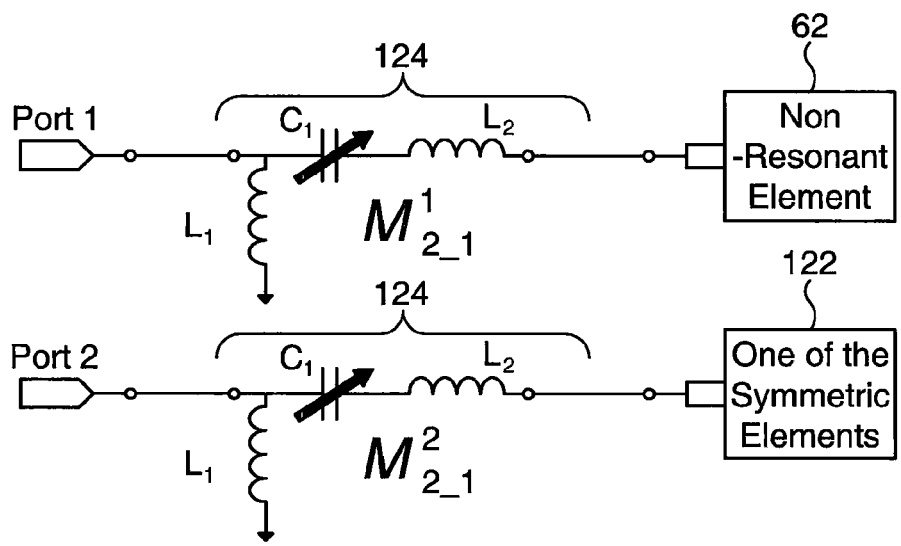
FIG. 20 shows a matching circuit arrangement for the antenna of FIGS. 19A and 19B.

FIG. 20 shows a matching circuit arrangement for the antenna 120 of FIGS. 19A and 19B. Thus, the non-resonant element 62 and one of the symmetrical arms 122 are connected to separate ports (Port 1, Port 2) via separate matching circuits 124. Each matching circuit 124 comprises of a variable capacitor $C_1$ and two fixed inductors $L_1$ and $L_2$.

The values of the components within each of the matching circuits 124 were calculated to optimise the return loss performance of the antenna 120. High isolation in this case, is achieved when both antennas 82, 62 are fed at the same vertical position (i.e. on the same transverse axis).

According to the above, embodiments of the present invention provide a reconfigurable antenna which is able to cover multiple cellular services such as DVB-H, GSM710, GSM850, GSM900, GSM1800, PCS1900, GPS1575, UMTS2100, Wifi®, Bluetooth®, LTE, LTA and 4G frequency bands. The antenna is also suitable for Cognitive Radio systems which might require a multi-resolution spectrum sensing function. The proposed antenna is therefore an ideal candidate for portable devices which require multi-service access, and is particularly well-suited to applications involving small terminals such as smart phones, laptops and PDAs.

It will be appreciated by persons skilled in the art that various modifications may be made to the above-described embodiments without departing from the scope of the present invention. In particular, features described in relation to one embodiment may be incorporated into other embodiments also.

The invention claimed is:

1. A reconfigurable antenna comprising:
  a balanced antenna and an unbalanced antenna, wherein the unbalanced antenna is mounted on a supporting substrate having an end and a conductive ground plane extending across the supporting substrate but not extending across the end, the unbalanced antenna being laterally spaced from the conductive ground plane by a gap, and the unbalanced antenna consisting of a single non-resonant element that is etched onto the supporting substrate and fed against the conductive ground plane,
  wherein both the balanced antenna and the unbalanced antenna are located substantially at the end of the substrate,
  wherein the balanced antenna comprises a pair of arms with respective first portions extending away from each other along the end of the substrate and respective second portions extending from ends of the respective first portions along sides of the end of the substrate so as to define a footprint at the end of the substrate,
  wherein each of the balanced and the unbalanced antenna is provided with at least one matching circuit including at least one variable capacitor to tune a frequency of the respective antenna over a particular frequency range to a desired operating frequency, the at least one matching circuit for the balanced antenna being coupled to a first signal port and the at least one matching circuit for the unbalanced antenna being coupled to a second signal port, and
  wherein the unbalanced antenna is at least partially enclosed by the footprint of the balanced antenna.

2. The antenna according to claim 1, wherein the antenna is configured to cover one or more of: DVB-H, GSM710, GSM850, GSM900, GSM 1800, PCS1900, GPS1575, UMTS2100, Wi-Fi®, Bluetooth®, LTE, LTA or 4G frequency bands.

3. The antenna according to claim 1, wherein different modes of operation are available by selecting different matching circuits for at least one of the balanced antenna or the unbalanced antenna, and wherein switches are provided to select a desired matching circuits for a particular mode of operation.

4. The antenna according to claim 1, wherein the respective at least one variable capacitor of at least one of the balanced antenna or the unbalanced antenna is constituted by multiple fixed capacitors with switches, a varactor or a MEMs capacitor.

5. The antenna according to claim 1, wherein at least one of each signal port or each matching circuit is associated with a different polarisation.

6. The antenna according to claim 1, wherein the balanced antenna and the unbalanced antenna are provided with substantially centrally located feed lines.

7. The antenna according to claim 1, wherein the unbalanced antenna is bracket-shaped having a first element substantially parallel to the substrate and a second element substantially perpendicular to the substrate.

8. The antenna according to claim 1, wherein the pair of arms of the balanced antenna comprises two inwardly facing L-shaped arms.

9. The antenna according to claim 8, wherein the balanced antenna is bracket-shaped with each arm having at least one perpendicular element.

10. The antenna according to claim 8, wherein a first arm is configured as a floating ground plane for a second arm.

11. The antenna according to claim 10, wherein the at least one matching circuit for the balanced antenna is mounted on the floating ground plane.

12. The antenna according to claim 1, wherein the balanced antenna is constituted by a printed dipole.

13. The antenna according to claim 1, wherein the substrate is substantially rectangular but with a cut-out located beneath the balanced antenna.

14. The antenna according to claim 1, wherein the balanced antenna and the unbalanced antenna are provided on opposite surfaces of the substrate.

15. The antenna according to claim 1, wherein the conductive ground plane is printed on a first surface of the substrate, and wherein the unbalanced antenna is also provided on the first surface.

16. The antenna according to claim 1, wherein a 90 degree phase difference is provided between each signal port or matching circuit at the respective desired operating frequency, the antenna further comprising a control system which is connected to each port and which is configured to select a desired operating mode.

17. The antenna according to claim 1, wherein the antenna is configured as a chassis antenna for use in a portable device or configured for Multiple-Input-Multiple-Output (MIMO) applications.

18. The antenna according to claim 1, wherein the substrate is constituted by a printed circuit board.

19. The antenna according to claim 1, wherein the balanced antenna is fed against a floating ground plane.

20. The antenna according to claim 19, wherein the at least one matching circuit for the balanced antenna is mounted on the floating ground plane.

21. A portable electronic device comprising:
  a reconfigurable antenna, wherein the reconfigurable antenna comprises:
    a balanced antenna and an unbalanced antenna, wherein the unbalanced antenna is mounted on a supporting substrate having an end and a conductive ground plane extending across the supporting substrate but not extending across the end, the unbalanced antenna being laterally spaced from the conductive ground plane by a gap, and the unbalanced antenna consisting of a single non-resonant element that is etched onto the supporting substrate and fed against the conductive ground plane, wherein both the balanced antenna and the unbalanced antenna are located substantially at the end of the substrate, wherein the balanced antenna comprises a pair of arms with respective first portions extending away from each other along the end of the substrate and respective second portions extending from ends of the respective first portions along sides of the end of the substrate so as to define a footprint at the end of the substrate, wherein each of the balanced and the unbalanced antenna is provided with at least one matching circuit including at least one variable capacitor to tune a frequency of the respective antenna over a particular frequency range to a desired operating frequency, the at least one matching circuit for the balanced antenna being coupled to a first signal port and the at least one matching circuit for the unbalanced antenna being coupled to a second signal port, and wherein the unbalanced antenna is at least partially enclosed by the footprint of the balanced antenna.

* * * * *